United States Patent
Breitenbach et al.

(10) Patent No.: US 6,547,997 B1
(45) Date of Patent: Apr. 15, 2003

(54) METHOD FOR PRODUCING SOLVENT-FREE NONCRYSTALLINE BIOLOGICALLY ACTIVE SUBSTANCES

(75) Inventors: Jörg Breitenbach, Mannheim (DE); Ulrich Reinhold, Speyer (DE); Jürgen Zeidler, Mutterstadt (DE); Jörg Rosenberg, Ellerstadt (DE)

(73) Assignee: Abbot Laboratories, Abbott Park, IL (US)

( * ) Notice: Subject to any disclaimer, the term of this patent is extended or adjusted under 35 U.S.C. 154(b) by 0 days.

(21) Appl. No.: 09/554,215
(22) PCT Filed: Nov. 9, 1998
(86) PCT No.: PCT/EP98/07141
§ 371 (c)(1), (2), (4) Date: May 11, 2000
(87) PCT Pub. No.: WO99/27891
PCT Pub. Date: Jun. 10, 1999

(30) Foreign Application Priority Data

Nov. 28, 1997 (DE) .......................... 197 52 895

(51) Int. Cl.[7] ............................. B29C 47/00
(52) U.S. Cl. ................... 264/85; 264/102; 264/349
(58) Field of Search .................... 264/85, 102, 349; 424/489

(56) References Cited

U.S. PATENT DOCUMENTS

| 4,578,455 | A |   | 3/1986 | Pipper et al. |
| 5,667,807 | A | * | 9/1997 | Hurner et al. ............. 424/455 |
| 5,789,436 | A | * | 8/1998 | Kato et al. ................. 514/443 |
| 5,811,547 | A |   | 9/1998 | Nakamichi et al. |
| 6,260,995 | B1 | * | 7/2001 | Schuchardt ................. 366/300 |

FOREIGN PATENT DOCUMENTS

| CA | 2208495 | 12/1997 |
| DE | 33 10 676 | 9/1984 |
| EP | 665 009 | 8/1995 |
| EP | 813 904 | 12/1997 |
| WO | 95/01321 | 1/1995 |
| WO | 97/18839 | 5/1997 |

* cited by examiner

Primary Examiner—Mark Eashoo
(74) Attorney, Agent, or Firm—Keil & Weinkauf

(57) ABSTRACT

Solvent-free noncrystalline bioactive substances are prepared from the corresponding crystalline bioactive substances in an extruder by melting the substances in the extruder under reduced pressure and in the absence of auxiliaries, cooling and comminuting.

12 Claims, No Drawings

METHOD FOR PRODUCING SOLVENT-FREE NONCRYSTALLINE BIOLOGICALLY ACTIVE SUBSTANCES

The present invention relates to a process for preparing solvent-free noncrystalline bioactive substances from the corresponding solvent-containing crystalline substances in an extruder.

It is frequently possible for one and the same chemical substance to form solids based on different order states. This situation is referred to as polymorphism and can likewise be influenced by the novel process. The various crystallographic forms also include pseudopolymorphic forms. These are ones in which not only the relevant substance but also foreign substances are involved in the structure due to formation of mixed crystals, solvates or hydrates. Mixed crystals are crystals composed of two or more chemical substances, and the components involved together form a specific crystallographic structure. Solvates and hydrates are to be regarded as special cases in which one of the components of the mixture is a solvent, with hydrates being formed with water.

Hydrates are particularly important. Because of the strict structural conditions, they have a stoichiometric structure and often show significantly poorer dissolving behavior than the anhydrous forms, because the water of crystallization is able to saturate additional secondary valencies in the molecular assemblage. The latter are unable in some circumstances, for steric reasons, to undergo saturation in the anhydrous form. This means that forms containing water of crystallization often have greater thermodynamic stability.

Many bioactive substances contain solvents as a result of the process for their preparation.

However, it is often difficult to remove such solvents, especially solvents bound in the crystal, by conventional processes such as heating or freeze drying.

It is to this extent of interest to provide a process for converting bioactive substances into a solvent-free form in a simple manner.

It is also known that the bioavailability of substances is frequently less good in their crystalline form than in the corresponding amorphous form.

EP-A 0 665 009 discloses a process in which active substances are converted in a twin screw extruder from one morphological state into another. However, this does not disclose the use of reduced pressure, nor does the process indicate how to proceed with active substances which contain water of crystallization or solvents.

It is an object of the present invention to provide a process for preparing solvent-free noncrystalline, ie. amorphous, bioactive substances from the corresponding solvent-containing crystalline bioactive substances.

We have found that this object is achieved by a process for preparing noncrystalline bioactive substances, which comprises melting the crystalline solvent-containing substances in an extruder in the absence of auxiliaries, the pressure being reduced in one zone of the extruder.

It is possible according to the invention to employ for this purpose not only pharmaceutical active substances but also a large number of bioactive substances which, by their nature, have solvent bound in their crystal lattice or else are merely moistened with a solvent.

The novel process is suitable, for example, for formulating the following substances or their physiologically acceptable salts antiinfectives aciclovir, aminoglycosides, amphotericin B, azole antimycotics, clotrimazole, itraconazole, sepraconazole, clindamycin, cephalosporins, chloramphenicol, erythromycin, 5-fluorouracil, etoposide, flucytosine, ganciclovir, griseofulvin, gyrase inhibitors, isoniazid, lincosamides, mebendazole, mefloquine, metronidazole, nitroimidazoles, novobiocin, platinum compounds, polymyxin B, praziquantel, pyrimethamine, rifamipicin, saquinavir, streptomycin, sulfonamides, tetracyclines, trimethoprim, vancomycin, zidovudine;

antipyretics, analgesics, antiinflammatory agents, paracetamol, ibuprofen, ketoprofen, oxaprozin, acetylsalicylic acid, morphine, propoxyphene, phenylbutazone;

antibiotics rifampicin, griseofulvin, chloramphenicol, cycloserine, erythromycin, penicillins such as penicillin G, streptomycin, tetracycline;

antiepileptics hydantoins, carbamazepine;

antitussives and antiasthmatics diphenhydramine;

antirheumatics chloroquine, indomethacin, gold compounds, phenylbutazone, oxyphenbutazone, penicillamine;

hypnotics barbiturates, phenobarbital, zolpidem, dioxopiperidines, ureides;

insecticides aldrin, dieldrin, chlorophenotane, hexachlorocyclohexane;

herbicides vinclozolin, strobilurins;

psychopharmaceuticals, neuroleptics perazine, promazine, sulpiride, thioridazine, chlorpromazine meprobamate, triflupromazine, melperone, clozapine, risperidone, reserpine;

tranquillizers;

antidepressants imipramine, paroxetine, viloxazine, moclobemide;

psychotonics;

psychomimetics;

diuretics potassium canrenoate, loop diuretics, furosemide, hydrochlorothiazide, spironolactone, thiazides, triamterene;

hormones androgens, antiandrogens, gestagens, glucocorticoids, oestrogens, cortisol, dexamethasone, prednisolone, testosterone, Adiuretin, oxytocin, somatropin, insulin;

immunosuppresants ciclosporin;

bronchodilators;

muscle relaxants, tranquilizers carisoprodol, tetrazepam, diazepam, chlordiazepoxide;

enzymes lipase, phytase;

gout remedies allopurinol, colchicine;

anticoagulants coumarins;

antiepileptics phenytoin, phenobarbital, primidone, valproic acid, carbamazepine;

antihistamines chlorphenoxamine, dimenhydrinate;

antimimetics;

antihypertensives, antiarrhythmics lidocaine, procainamide, quinidine, calcium antagonists, glycerol trinitrate, isosorbide dinitrate, isosorbide 5-mononitrate, pentaerythrityl tetranitrate, nifedipine, diltiazem, felodipine, verapamil, reserpine, minoxidil, captopril, enalapril, lisinopril;

sympathomimetics norfenefrine, oxedrine, midodrine, phenylephrine, isoprenaline, salbutamol, clenbuterol, ephedrine, tyramine, β blockers such as alprenolol, metoprolol, bisoprolol;

antidiabetics biguanides, sulfonylureas, carbutamide, tolbutamide, glibenclamide, metformin, acarbose, troglitazone;

iron preparations;

vitamins vitamin C, B, A, D, folic acid;

ACE inhibitors captopril, ramipril, enalapril;

anabolics;

iodine compounds;

X-ray contrast agents;

CNS-active compounds;

antiparkinson agents biperiden, benzatropine, amantadine, opioid analgesics, barbiturates, benzodiazepines, disulfiram, lithium salts, theophylline, valproate, neuroleptics;

cytostatics;

antispasmolytics;

vasodilators naftidrofuryl, pentoxifylline.

It is also possible to employ mixtures of bioactive substances. Amorphous solids have, like liquids, a high dissolving capacity for mixing partners. It is therefore possible for one bioactive substance to dissolve another in the melt. This may lead to mixing diagrams with eutectics. Depending on the position of the melting curves, one or other substance may be present as crystals at the same time as the amorphous first substance.

Preferred substances are those mentioned in the list or those which contain organic solvents and/or water from a crystallization process. This also applies to vitamins.

Preferred active substances for the novel process are amiloride HCl.2H$_2$O, amoxicillin.3H$_2$O, ampicillin.3H$_2$O, atropine sulfate.1H$_2$O, benzylpenicillin benzathine.1H$_2$O, calcium folinate.5H$_2$O, carbidopa.1H$_2$O, cefepime.1H$_2$O, cefixime.3H$_2$O, ceftazidime.5H$_2$O, cephaclor.1H$_2$O, cephalexin.1H$_2$O, quinidine sulfate.4H$_2$O, quinine sulfate.2H$_2$O, clindamycin HCl.H$_2$O, codeine phosphate.½H$_2$O, cyclophosphamide.1H$_2$O, dihydralazine sulfate.2½H$_2$O, doxycycline.1H$_2$O, doxycycline.½C$_2$H$_5$OH.½H$_2$O, iron(II) gluconate.2H$_2$O, iron(II) sulfate.1H$_2$O, flucloxacillin sodium.1H$_2$O, G-strophanthin.8H$_2$O, ipratropium bromide.1H$_2$O, lidocaine HCl.1H$_2$O, lincomycin HCl.1H$_2$O, loracarbef.1H$_2$O, mepacrine 2HCl.2H$_2$O, metamizole sodium.1H$_2$O, methyldopa.1½H$_2$O, minocycline HCl.2H$_2$O, morphine sulfate.5H$_2$O, sodium ibuprofenate.2H$_2$O, sodium picosulfate.1H$_2$O, oxyphenbutazone.1H$_2$O, pyritinol 2HCl.1H$_2$O, sultamicillin tosilate.2H$_2$O, theophylline ethylenediamine.2H$_2$O or vinblastine sulfate.1H$_2$O or mixtures thereof.

The amount of solvent in these cases may vary within a wide range. Thus, active substances used in pharmacy are known with low solvent contents<1% by weight. However, in the chemical synthesis of the active substances, despite drying, the bioactive substance may become moist so that solvent contents of more than 10% by weight are found.

The novel bioactive substances are prepared using shear forces and with input of thermal energy. The mixing preferably takes place in a single screw or multiscrew extruder, particularly preferably a twin screw extruder. A melt of the bioactive substance is produced by thermal energy input. This normally takes place by heating the extruder casing to 35–350° C. The process temperature depends on the melting point of the substance or mixture of substances.

The molten bioactive substance or the mixture of molten bioactive substances is conveyed by the movement of the screw toward the extruder outlet, which is preferably a die.

However, the extrusion can also according to the invention take place from the open extruder. There is then a fall in pressure in the last section.

Depending on the viscosity of the melt and the screw geometry, the operating pressure in the extruder zones which are located upstream of the zone equipped for reducing the pressure, such as extruder channel, can be from 1 to 500 bar. Pressures from 3 to 60 bar are preferred.

It is preferred according to the invention for the pressure in the last segment or section (zone of the extruder) before the die or the end of the extruder channel to be from 10 to 600 mbar, preferably 30–400 mbar, particularly preferably 50–100 mbar. The solvent is stripped out of the melt in this reduced-pressure segment. The result is an amorphous mass which can be converted into a powder by cooling in another segment and the use of shear forces which can be introduced, for example, via particular screw configurations. It is thus possible also to discharge the melt and then cool it and subsequently grind it.

Such powders of bioactive substances are suitable for pharmaceutical and cosmetic preparations, but also for use in the food, feed and veterinary sectors.

The bioactive substance is particularly preferably in the form of an amorphous powder.

Unambiguous assessment of the state of a powdered material is possible only with the aid of X-ray fine-structure investigation. The investigation methods are based on the fact that interference effects occur when X-ray light is passed through an ordered material. Phase transformations, ie. changes in the state of the material as a function of temperature, can be observed with the aid of thermal analytical methods such as differential thermal analysis and differential scanning calorimetry. They provide important indications of the possible behavior of an active substance during processing.

The screw geometry in the extruder heating zone in which the mixing and melting take place can be chosen to be closely intermeshing, intermeshing or nonintermeshing, with closely intermeshing screw geometry being preferred. The screws may rotate in the same direction or, preferably, in opposite directions. In the mixing and melting region, besides conveying elements there are preferably mixing and kneading elements arranged on the screws. Conveying elements are single- and multi-flight screw elements which differ in pitch. Mixing elements are gear-like toothed disk elements or backward-conveying elements provided with perforations, it being possible for some of the perforations to extend as far as the screw root or take up at least half of the helical radius. Kneading elements are bicuspid or tricuspid disks, with the elements always having a plurality of disks which differ in width and have a defined angle of offset to one another. The jacket of the cooling zone is cooled with liquid coolant. The temperature in the conveying zone of the cooling zone is preferably-adjusted to be 5°–30° Celsius below the softening point of the composition to be cooled. It is possible for the temperature to be reduced over the entire cooling zone in the direction of flow by up to 150° Celsius below the softening point, depending on the softening point of the composition. It may also be advisable for shock cooling to take place in the mixing region of the cooling zone and to cool the jacket to temperatures in the range from –10° Celsius to +10° Celsius.

The detailed screw geometry also depends on the melting point of the substances to be processed.

It is possible with the aid of the novel process to prepare compositions with particle sizes in the range from 0.0001 to 50 mm diameter. Depending on the choice of the screw diameter, of the mixing and kneading elements and of the speeds of rotation of the screw, the resulting particles have sizes in the range 10–50 mm, 1–3 mm, 0.3–1 mm, 0.1–0.3 mm, 0.03–0.1 mm or 0.001–0.03 mm. The particle sizes are preferably 0.001–10 mm, particularly preferably 0.005–3 mm. The particle sizes adjusted in the specific case depend in particular on the area of use required. The particulate preparations show good uniformity in the particle size distribution so that they can be processed further without other screening processes.

The compositions according to the invention can be processed to tablets, suppositories, granules, instant granules, pellets, implants, floating tablets or be used to fill capsules.

PREPARATION EXAMPLES

The extrudates were prepared using a corotating, intermeshing twin-screw extruder (ZSK 30 from Werner & Pfleiderer, Stuttgart, Germany) consisting of 8 separate chamber-like zones which could be heated and cooled. These zones are referred to hereinafter as "zone 1", "zone 2", etc., with the starting material entering at zone 1 and emerging at zone 8. Zone 1 was cooled with water (outflowing water at 30° Celsius). Throughout the test, zone 2 was operated at 200° Celsius and zones 3 and 4 at 210° Celsius. Zone 4 contained an attachment for reducing the pressure to 150 millibar. Zones 5, 6, 7 and 8 were cooled with water, the resulting outflowing water being at 40° Celsius, 30° Celsius, 25° Celsius and 20° Celsius, respectively.

Example 1

Preparation of an Amorphous Sodium Ibuprofenate 1700 g of sodium ibuprofenate dihydrate were fed per hour through belt weigh feeders equipped with screws rotating at 36 revolutions per minute into zone 1 of this extruder. The extruder was operated for 10 hours. The ibuprofenate was then in the form of an amorphous anhydrous mass.

Example 2

Sodium ibuprofenate obtained from a crystallization process and containing 2% by weight of water and 2% by weight of methanol was processed as in Example 1. An amorphous solvent-free powder was obtained.

We claim:

1. A process for preparing a solvent-free noncrystalline bioactive substance from the corresponding solvent-containing bioactive substance crystals in an extruder, wherein the solvent-containing substance crystals are melted in the extruder under reduced pressure, the pressure being reduced in one zone of the extruder, and wherein the substance crystals are employed free of auxiliary substances.

2. A process as claimed in claim 1, which is carried out under inert gas.

3. A process as claimed in claim 2, wherein the inert gas is nitrogen.

4. A process as claimed in claim 1, wherein the solvent is integrated into the crystal lattice of the bioactive substance.

5. A process as claimed in claim 4, wherein the solvent is water.

6. A process as claimed in claim 4, wherein the solvent is an organic solvent.

7. A process as claimed in claim 1, wherein more than one bioactive substance is employed.

8. The process of claim 1, wherein the reduced pressure is from 10 to 600 mbar.

9. The process of claim 8, wherein the solvent-containing substance crystals are melted at from 35 to 350° C.

10. The process of claim 1, wherein the reduced pressure is from 30 to 400 mbar.

11. The process of claim 1, wherein the reduced pressure is from 50 to 100 mbar.

12. The process of claim 1, wherein the solvent-containing substance crystals are melted at from 35 to 350° C.

* * * * *